United States Patent [19]

Laerdal

[11] 4,005,709
[45] Feb. 1, 1977

[54] COMPRESSION BANDAGE

[76] Inventor: Asmund Sigurd Laerdal, Stavanger, Norway

[22] Filed: Apr. 2, 1976

[21] Appl. No.: 673,094

[30] Foreign Application Priority Data

Apr. 11, 1975 Germany ............... 2515786

[52] U.S. Cl. ................ 128/155; 128/156
[51] Int. Cl.² ..................... A61F 13/00
[58] Field of Search ............ 128/155, 156, 325

[56] References Cited

UNITED STATES PATENTS

| | | | |
|---|---|---|---|
| 2,858,830 | 11/1958 | Robins | 128/156 |
| 3,490,448 | 1/1970 | Grubb | 128/156 |
| 3,888,247 | 6/1975 | Stenvall | 128/155 |
| 3,927,669 | 12/1975 | Glatt | 128/156 |

*Primary Examiner*—John D. Yasko
*Attorney, Agent, or Firm*—Marn & Jangarathis

[57] ABSTRACT

A compression bandage includes a bandage strip with an absorbent layer on one side. A pressure piece of slightly deformable and slightly absorbent molded material is attached to the other side of the strip opposite the absorbent layer. When the bandage is applied and the strip wound around the injured part, the pressure pad exerts pressure through the strip and absorbent layer onto the wound, and cannot slip from the correct position.

12 Claims, 4 Drawing Figures

COMPRESSION BANDAGE

The invention relates to a compression bandage of the type with a pressure piece provided, and particularly intended for application to bleeding wounds.

A compression bandage has been proposed in which a roll-shaped pressure pad with an insulated core is sewn onto the bandage. Such a compression bandage is relatively complicated to manufacture, and the core is surrounded by absorbent material, so that it is possible for the pressure pad to become saturated with blood. Also, the pressure pad only, of the bandage, is available for covering the wound and, when the bandage is applied in the correct manner, only a relatively small region of the cirumference of the pressure pad lies on the wound and thus the wound is not necessarily completely and hygienically closed. If it is desired to eliminate this difficulty by using additional bandaging material, then correct application of the compression bandage is usually too difficult for untrained personnel.

In another proposed compression bandage, a flexible foam rubber cushion and a pressure plate are joined firmly to a bandage strip. However, this compression bandage has the disadvantage that pressure is not exerted solely at the required point, and that blood vessels which are immediately adjacent to the wound but which have not been damaged are constricted. This can result in serious and permanent damage.

It is an aim of the invention to provide a compression bandage which at least reduces these problems.

According to the present invention there is provided a compression bandage including a bandage strip, consisting of molding of slightly deformable and slightly absorbent material firmly attached to one side of the strip, and an absorbent layer on the other side of the strip in the region of the pressure piece.

The compression bandage of the invention can generally be applied easily by untrained personnel or even by the injured person, does not absorb blood to an excessive extent but enables complete, hygienic closure of the wound to be achieved. The pressure effect which can be achieved is also somewhat improved compared with prior compression bandages.

Preferably, the cross-section of the moulding increases outwards from the base surface fastened to the bandage. Preferably, the molded piece consists of foamed plastics material, preferably polystyrene foam.

Thus, in the compression bandage according to the invention an absorbent layer is provided on the opposite side of the bandage to the pressure piece. The result is that, when the compression bandage is applied, the absorbent layer is pressed by the bandage onto the wound and the adjacent region in such a way that the wound is perfectly closed. Despite this, there is no danger that the molded piece which serves as the pressure piece, will slip during application of the bandage since it is fastened on the other side of the bandage from the absorbent layer. The design of the compression bandage according to the invention provides that, since the molded piece can absorb to only a small extent if at all, only a slight absorption of blood by the bandage is to be expected, and it is very unlikely that blood will reach the side of the moulding remote from the wound. The use of the somewhat deformable, that is to say relatively hard, and, in addition, precisely shaped pressure piece in place of the roll-like, soft pressure pad of the known compression bandage has the advantage that the pressure piece can adjust, to a certain extent, to the shape of the part of the body to which the bandage is to be applied, while still providing an appropriate pressure effect. Due to the relative hardness of the molded piece blood can still circulate around the wound, which is not the case when a soft pad is used. The compression bandage of the invention can be manufactured very easily since it is not necessary to provide a core with a covering. It is necessary only to fasten an absorbent layer, for example a cotton-wool layer provided with a covering layer, onto one side of the bandage strip by any means and to fasten the molded piece onto the other side, it being advantageous for both the absorbent layer and the molded piece to be adhered to the bandage. The use of a molded piece which is separated from the absorbent layer by the strip also allows the shape of the pressure piece to be varied according to particular requirements and the use, with the same bandage strip and the same material, different materials for the molded piece, for example materials of varying hardness.

it is advantageous for the longitudinal and cross-sections of the molded piece to be approximately trapezium shaped, the shorter parallel side of each cross-section being adjacent to the bandage strip. This has the advantage that the region over which the molded piece presses onto the wound is precisely limited and moreover, due to the top surface being larger than the surface fastened to the bandage strip, provision is made for compression forces to be introduced approximately vertically to the wound. In plan view, the moulding can be rectangular, with its long axis transverse of the longitudinal axis of the bandage strip. Alternatively, in plan view the molded piece may have a round or oval shape.

The effect of introducing the forces approximately vertical to the wound can be further improved if the top surface, which faces away from the bandage strip, of the moulding has a convex curvature.

In order to prevent compression of blood vessels or the like, it is further proposed, according to the invention, that the edges and/or corners of the molded piece be rounded off, at least on the side which faces the bandage strip.

In itself, the bandage strip can be of any known type. However, it is particularly advantageous for it to be elastically extendable in the longitudinal direction. The bandage strip may have a self-adhesive finish. In this context "self-adhesive" is to be understood to mean that the bandage is such that two adjacent layers can remain adhering to one another without the use of special fastening elements. This can be achieved, for example, by a layer of latex on the bandage. One appropriate product is marketed by the 3M Company, St. Paul, Minn., U.S.A. under the tradename "COBAN". This is a bandage which comprises a non-woven polyester fibre base material, elastic threads running in the longitudinal direction and a layer of latex. The advantage provided by the use of such a self-adhesive bandage is that no further special fastening is necessary after the bandage has been applied and this makes it possible for an injured person to apply the bandage to himself if necessary.

The invention will be more clearly understood from the following description which is given by way of example only with reference to the accompanying drawings, in which.

The drawings show a compression bandage having a bandage strip 1 which is elastically extendable in the longitudinal direction and which also has a self-adhesive finish. This strip may be the product which is marketed under the tradename "COBAN" by the 3M Company, St. Paul, Minn. U.S.A. and which consists of polyester fibres, elastic threads running in the longitudinal direction and a layer of latex.

Figure 1:
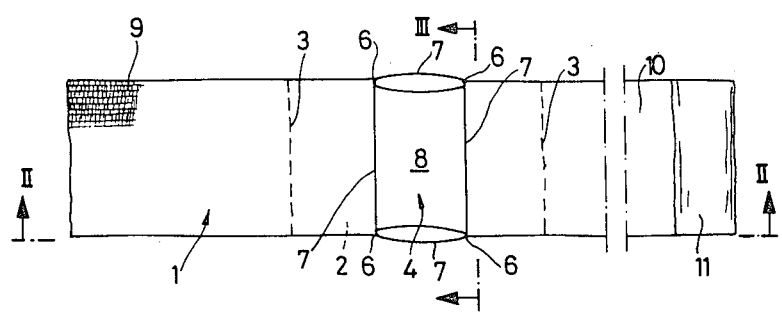
FIG. 1 is a plan view of a compression bandage according to the invention.

An absorbent layer 2, which in FIG. 1 is indicated by the broken line 3, is adhered (see FIGS. 2 and 3) on the underside of the bandage 1. The aborbent layer 2 may be, for example, cotton wool which has a covering so that it keeps its shape.

The lower, smaller basal surface 5 of a moulding 4 is also adhered onto the bandage 1 on the opposite side from the layer 2 in the region thereof. As shown, the molded piece 4 consists of polystyrene foam so that when appropriate pressure is applied it can be deformed to a certain extent in order to adapt to the area of the wound.

As also shown in the drawings, the molded piece 4 is approximately trapezoidal in both longitudinal section and in transverse cross-section. Its corners 6 and edges 7, particularly the edges 7 adjoining the basal surface 5, are rounded off. Moreover, the top surface 8, which is opposite the smaller basal surface 5, has a convex curvature.

It is not necessary for the molded piece 4 to have, in plan view, the approximately rectangular shape shown. It can also be for instance oval, or, in particular, circular in plan view although, nevertheless, the cross-section should preferably be approximately trapezoidal. Moreover, rounding off of the edges is appropriate in this case also.

Figure 2:
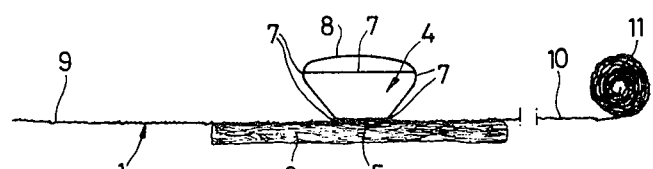
FIG. 2 is a side view of the bandage of FIG. 1 along line II—II in FIG. 1.
Figure 3:
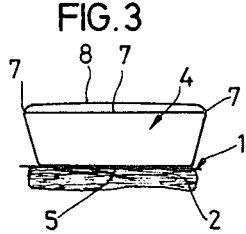
FIG. 3 is a cross-section through the bandage of FIG. 1 along line III—III.

FIGS. 1 and 2 show that the bandage strip 1 extends on both sides beyond the absorbent layer 2 and the region of the molded piece 4. To one side, 9, (on the left of the drawing) the strip is relatively short. When applying the compression bandage this end 9 serves only to provide a surface which enables the other end, 10, of the bandage to be taken up. In the drawing, the long, free end 10 of the bandage is still largely wound up in a roll 11.

Figure 4:
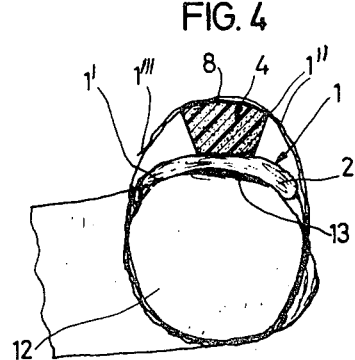
FIG. 4 is a schematic view and a section of a bandage, according to the invention, applied to a wound.

As can be seen from FIG. 4, in which an arm or the like, which has a wound 13, is shown in an extremely simplified foam as 12, only the absorbent layer 2 is pressed onto the wound 13 with a first layer 1' of the bandage strip 1 when the compression bandage is applied. At the same time the moulding 4, which is stuck onto the strip 1, is also located in the area above the wound 13, where it is to be fixed when the compression bandage is fully applied.

Several layers 1" of the bandage strip 1 are now wound round the part of the body, for example the arm 12, and the molded piece 4. Then, without the bandage strip 1 being extended in the longitudinal direction, the free end 1''' of the strip is simply laid onto the subjacent layer 1''of the strip, where, because of the self-adhesive design of the strip 1, it remains without special fasteners.

FIG. 4 shows that the wound 13 can be correctly covered and overlapped by the absorbent layer 2. At the same time, it can be seen from FIG. 4 that the moulding 4, which curves towards the wound, is able to achieve the desired pressure in an appropriate manner. The particular shape of the molded piece, especially its trapezoidal cross-section and the convex curvature of the upper outer surface 8, allows for the compression forces exerted by the layers 1' of the strip 1 on the moulding 4 to press the moulding 4 approximately perpendicularly onto the wound 13.

It will be appreciated that even unskilled personnel can apply the compression bandage according to the invention easily and in the correct manner. It is also clear that it is possible to manufacture the compression bandage according to the invention and to combine the individual parts (strip 1, layer 2 and moulding 4) without great difficulties.

A slightly deformable and slightly absorbent material, as required for the molded piece, is in general to be regarded as a material which, in respect of its deformability and absorptive capacity, has an effect equal or similar to that of polystyrene foam, such as is frequently used, for example, for packaging purposes.

I claim:

1. A compression bandage comprising a bandage strip having first and second sides, a pressure piece consisting of a molding of slightly deformable and slightly absorbent material firmly attached to said first side, and an absorbent layer fixed on said second side of said bandage strip in the region of said pressure piece whereby when the bandage is applied and the strip wound around the injured part, the pressure pad exerts pressure through the strip and absorbent layer onto the wound.

2. A compression bandage as claimed in claim 1, wherein, in area of cross-section parallel to said sides, the molded piece increases outwardly from said strip.

3. A compression bandage as claimed in claim 1, wherein said molded piece is of foamed plastics material.

4. A compression bandage as claimed in claim 1, wherein said molded piece is of polystyrene foam.

5. A compression bandage as claimed in claim 1, wherein in the longitudinal section and cross-section, the molded piece is approximately trapezoidal in shape, the trapezia having two parallel edges of which the shorter are in contact with said bandage strip.

6. A compression bandage as claimed in claim 1 and having, on said molded piece a top surface remote from the bandage strip which is of convex curvature.

7. A compression bandage as claimed in claim 1, wherein edges of the molded piece are rounded off, at least on the side of said moulding which is attached to said strip.

8. A compression bandage as claimed in claim 1, wherein corners of the molded piece are rounded off, at least on the side of said moulding which is attached to said strip.

9. A compression bandage as claimed in claim 1, wherein said molded piece is adhered to said bandage strip.

10. A compression bandage as claimed in claim 1, wherein said absorbent layer is adhered to said bandage strip.

11. A compression bandage as claimed in claim 1, wherein said bandage strip is elastically extendable in its longitudinal direction.

12. A compression bandage as claimed in claim 1, and having a self-adhesive finish to said bandage strip.

* * * * *